United States Patent [19]
Fischer et al.

[11] Patent Number: 5,545,815
[45] Date of Patent: Aug. 13, 1996

[54] CONTROL OF FRUIT RIPENING IN PLANTS

[75] Inventors: Robert L. Fischer; Linda J. Margossian, both of El Cerrito, Calif.; Lola Penarrubia, Valencia, Spain

[73] Assignee: The Regents of the University of California, Oakland, Calif.

[21] Appl. No.: 772,032

[22] Filed: Oct. 8, 1991

[51] Int. Cl.⁶ .......................... A01H 5/00; C12N 15/29; C12N 15/82; C12N 15/84
[52] U.S. Cl. .................. 800/205; 435/172.3; 435/320.1; 536/23.6; 536/24.5; 800/DIG. 44; 47/58
[58] Field of Search ........................ 435/172.3, 320.1; 536/27, 23.6, 24.5; 47/58, DIG. 1; 800/205, DIG. 44; 935/9, 11, 64, 67

[56] References Cited

U.S. PATENT DOCUMENTS 4,801,540  1/1989  Hiatt et al. .......................... 435/172.3

FOREIGN PATENT DOCUMENTS 9203562  3/1992  WIPO .......................... C12N 15/82
9206206  4/1992  WIPO .......................... C12N 15/82

OTHER PUBLICATIONS

Cleveland, T. E. et al. 1987 *Plant Molec. Biol.* vol. 8 pp. 199–207.
Van der Krol, A. R. et al. 1990. *Plant Molec. Biol.* vol. 14 pp. 457–466.
Boswell, D. R. et al. 1988. In *Computational Molecular Biology*, ed. A. M. Lesk, Oxford University Press, pp. 161–178.
Lieberman, *Ann. Rev. Plant Physol.* 30:533–591 (1979).
Biale and Young, *Recent Advances in the Biochemistry of the Fruits and Vegetables* (Friend and Rhodes, eds, Academic Press, London, 1981).
Lincoln et al., *Proc. Natl. Acad. Sci. U.S.A.* 84:2793–2797 (1987).
Lincoln and Fischer, *Mol. Gen. Genet.* 212:71–75 (1988).
Lincoln and Fischer *Plant Physiol.* 88:370–374 (1988).
Deikman and Fischer, *EMBO J.* 7:3315–3320 (1988).
Hamilton et al., *Nature* 346:284 (1990).
Herner, et al. *Plant Physiol.* 52:38–42 (1973).
Ng, et al., *J. Amer. Soc. Hort. Sci.* 102:504–509 (1977).
Bleecker, et al. *Science* 241:1086–1089 (1988).
Guzman, et al. *Plant Cell* 2:513–523 (1990).

*Primary Examiner*—Mary E. Mosher
*Attorney, Agent, or Firm*—Townsend and Townsend and Crew

[57] ABSTRACT

The present invention provides novel transgenic plants comprising antisense DNA constructs which inhibit expression of ethylene perception genes. The plants exhibit decreased levels of ethylene-mediated responses, such as fruit ripening.

11 Claims, 4 Drawing Sheets

CONTROL OF FRUIT RIPENING IN PLANTS

The Government has rights in this invention pursuant to Grant No. DCB 90-04353 awarded by the National Science Foundation.

BACKGROUND OF THE INVENTION

1. Field of the Invention

This invention relates generally to the use of recombinant DNA methods for genetically altering plants. In particular it relates to the control of ethylene-mediated responses in plants by inhibiting ethylene perception using antisense constructs.

The plant hormone ethylene has a profound influence on plant physiology. Active in trace amounts it affects a number of processes such as fruit ripening, seed germination, plant growth, leaf and flower senescence, pathogen infection, and the interaction of plants with their environment. For instance, ethylene is known to induce a number of physiological changes associated with fruit ripening such as accumulation of carotenoid figments, conversion of cholorplasts to chromoplasts, the increased expression of genes encoding cell wall degradation enzymes fruit softening and susceptibility to pathogens. The importance of ethylene in fruit ripening has been shown by experiments demonstrating that exposure of fruits to specific inhibitors of ethylene biosynthesis greatly retards ripening and that the onset of ripening is hastened when unripe mature green fruits are exposed to exogenous ethylene. Similarly, ethylene is known to promote abscision of leaves, flowers and fruits in a variety of plants species by triggering enzymes that cause cell wall dissolution associated with abscision.

Control of the effects of ethylene is a particularly useful approach to modulating such processes as senescence and fruit ripening. Previous efforts have focused on controlling the amount of ethylene produced by the plant. For example, mutations have been identified that result in production of lower amounts of ethylene during tomato fruit ripening. The fruits from these plants ripen more slowly, and have an extended shelf life. Lack of genetic diversity, however, has frequently limited the success of such breeding programs. Molecular approaches have focused on production of transgenic plants with reduced levels of enzymes required for ethylene biosynthesis. Because plants are extremely sensitive to ethylene, however, it is difficult to completely eliminate the response by reducing ethylene production. Thus, the prior art lacks useful methods for effectively controlling and minimizing the deleterious responses of plants to ethylene.

2. Background Art

The physiological responses of plants to ethylene are reviewed in Liberman, *Ann. Rev. Plant Physiol.* 30:533–591 (1979). The role of ethylene in the regulation of fruit ripening is described in Biale and Young, in *Recent Advances in the Biochemistry of the Fruits and Vegetables* (Friend and Rhodes, eds, Academic Press, London, 1981).

The cloning of mRNAs that increase in concentration as a result of exposure of tomato fruit to exogenous ethylene is described in Lincoln et al. *Proc. Natl. Acad. Sci. U.S.A.* 84:2793–2797 (1987). Expression of a gene, designated E8, has been shown to be responsive to ethylene and under strict developmental control (Lincoln and Fischer *Mol. Gen. Genet.* 212:71–75 (1988) and Lincoln and Fischer *Plant Physiol.* 88:370–374 (1988). The cDNA sequence of the E8 gene is disclosed in Deikman and Fischer, *EMBO J.* 7:3315–3320 (1988).

Hiatt et al., U.S. Pat. No. 4,801,340 describes the use if antisense constructs to inhibit polygalacturonase activity in tomato fruit. Transgenic plants have been produced with reduced levels of enzymes required for ethylene biosynthesis Hamilton et al., *Nature* 346:284 (1990).

Mutants have also been identified which show reduced responsiveness to ethylene. Herner, et al., *Plant Physiol.* 52:38–42 (1973); Ng, et al., *J. Amer. Soc. Hort. Sci.* 102:504–509 (1977); Bleecker, et al., *Science* 241:1086–1089 (1988); and Guzman, et al., *Plant Cell* 2:513–523 (1990).

SUMMARY OF THE INVENTION

The present invention relates to novel methods for inhibiting ethylene-mediated responses in plants. The methods comprise introducing into a plant an expression cassette having a plant promoter sequence operably linked to a nucleotide segment homologous to a subsequence of a gene encoding a polypeptide associated with ethylene perception. The nucleotide segment is linked to the promoter sequence in an antisense orientation so that expression of the targeted gene is decreased and the ethylene-mediated response is inhibited. The methods involve introducing the expression cassette into plants through in vitro techniques or through a sexual cross.

The invention also provides expression cassettes which can be used to transform plants according to the methods above. The promoter in the expression cassette can be either constitutive or inducible. The antisense nucleotide segment to be introduced into the plant may include the full length coding region of the targeted gene or a portion thereof. The segment is preferably homologous to a subsequence of the targeted gene, but exact correspondence between the introduced sequence and the sequence to be repressed is not required to effectively inhibit expression.

The invention further provides plants comprising the expression cassettes described above. Preferably, the plant is tomato and the ethylene-mediated response is fruit ripening. In tomato, a preferred target gene is E8.

DETAILED DESCRIPTION

The invention relates to the use of antisense regulation to control deleterious responses to ethylene in plants. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been shown that antisense RNA inhibits gene expression by preventing the accumulation of mRNA which encodes the protein of interest, see, e.g., Sheehy et al., *Proc. Nat. Acad. Sci.*, 85:8805–8809 (1988), and Hiatt et al., U.S. Pat. No. 4,801,340 which are incorporated herein by reference.

Of particular interest in the present invention are genes which encode polypeptides associated with ethylene perception in plants. As used herein, "ethylene perception" refers to the detection of ethylene and the mediation of the initial biochemical responses to ethylene in plant cells. Genes involved in ethylene perception include, but are not limited to, those encoding receptor molecules that detect the presence of ethylene and/or initiate physiological processes in response to ethylene, as well those genes that encode enzymes involved in the synthesis of these molecules.

Such genes are typically identified functionally in that inhibition of their expression leads to an inability of plant tissues to respond to ethylene as measured by a variety of physiological parameters. Ethylene perception genes can be identified using subtraction hybridization procedures to identify ethylene-inducible sequences. Antisense ethylene-inducible sequences are placed in expression cassettes and tested for the ability to inhibit ethylene responses in transgenic plants.

Alternatively, the presence of restriction fragment length polymorphisms (RFLP) between wild type and mutant varieties can be used to identify the desired sequences.

The term "ethylene-mediated response" as used herein includes fruit ripening, seed germination, plant growth, abscission, leaf and flower senescence, pathogen infection, disease induced by pathogen infection, and the like. For a review of the effects of ethylene on plant physiology, see, *Ethylene and Plant Development* Roberts and Tucker, eds. (Butterworths, London, 1985), which is incorporated herein by reference.

1. General Methods

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory. Manual,* Cold Spring Harbor Laboratory, Cold Spring Harbor, N.Y., (1989), which is incorporated herein by reference.

The general techniques used to prepare the recombinant constructs comprising antisense sequences capable of inhibiting ethylene perception are known to those skilled in the art. The manipulations outlined in detail below typically involve preparing a cDNA library enriched for ethylene-inducible sequences using subtraction hybridization procedures. The library is then screened using probes enriched for ethylene-inducible sequences. Next, expression cassettes comprising a plant promoter and other sequences necessary for expression of antisense ethylene-inducible sequences are prepared. The are linked to the promoter in the antisense direction. The appropriate host plant cells are then transformed with the expression cassettes and plants transcribing the antisense sequences are regenerated. The regenerated plants displaying a reduced response to ethylene are selected.

2. Preparation of Libraries

Genomic or cDNA libraries are prepared according to standard techniques as described, for instance, in Sambrook, supra. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and cosmids.

In the present invention, cDNA libraries enriched for ethylene inducible sequences are generally used to screen for the desired sequences. Preparation of appropriately enriched cDNA libraries from ripening tomato fruit is described in Lincoln et al. *Proc. Natl. Acad. Sci. U.S.A.* 84:2793–2797 (1987), which is incorporated herein by reference. Briefly, mRNA from ripening tomato fruit is isolated and cDNA is prepared. Short chains of oligo d-T nucleotides are hybridized with the poly-A tails of the mRNA and serve as a primer for the enzyme, reverse transcriptase, which synthesizes a complementary DNA (cDNA) strand. The cDNA is enriched for the desired sequences using subtraction hybridization procedures by labelling the cDNA and hybridizing it with mRNA from unripe fruit according to the procedures in Davis et al. *Proc. Natl. Acad. Sci. U.S.A.* 81:2194–2198 (1984), which is incorporated herein by reference.

Unreacted cDNA is isolated and used to prepare a library for screening. To do this, a second DNA strand is synthesized using the first cDNA strand as a template. Linkers are added to the double-stranded cDNA for insertion into a plasmid or λ phage vector for propagation in *E. coli*.

Identification of clones harboring the ethylene-inducible sequences is performed by either nucleic acid hybridization or immunological detection of the encoded protein, if an expression vector is used. Typically, oligonucleotide probes specific for ethylene-inducible genes are used. In the case of probes from tomato fruit, these probes are isolated from labeled cDNA prepared from unripe fruit treated with ethylene. The ethylene inducible sequences are identified by hybridizing with mRNA from unripe fruit. Unreacted labeled cDNAs are isolated and used to probe the cDNA library.

Oligonucleotide probes useful for identification of ethylene-inducible genes can also be prepared from conserved regions of related genes in other species. For instance, probes derived from the E8 gene may be used to screen libraries for related genes in other species. The probes derived from the E8, or other ethylene perception genes, can also be used to locate other members of the appropriate gene family in the same species. The probes are typically used to identify sequences that hybridize under stringent conditions to ensure that the sequences are in fact related. Typically, stringent conditions suitable for finding related sequences would be performing the hybridization at room temperature using 1M salt.

3. Vector Construction

Selection of an appropriate vector useful in initiating transcription of antisense transcripts which inhibit ethylene perception is relatively simple, as the constraints are minimal. The minimal requirements of the vector are that the desired nucleic acid sequence be introduced in a relatively intact state. Thus, any vector which will produce a plant carrying the introduced DNA sequence should be sufficient. Any vector which will introduce a substantially intact RNA which can ultimately be converted into a stably maintained DNA sequence is also acceptable.

Even a naked piece of DNA would be expected to be able to confer the properties of this invention, though at low efficiency. The decision as to whether to use a vector, or which vector to use, will be guided by the method of transformation selected. This determination is considered to be well with in the ordinary skill of those in the art.

The vectors useful in the present invention include, but are not limited to, the Ti plasmid vectors, shuttle vectors designed to maximally yield high numbers of copies, episomal vectors containing minimal sequences necessary for ultimate replication once transformation has occurred, and viral vectors, including the possibility of RNA forms of the gene sequences. The selection of vectors and methods to construct them are commonly known to persons of ordinary skill in the art and are described in general technical references (See, in general, *Methods in Enzymology* Vol. 153 ("Recombinant DNA Part D") 1987, Wu and Grossman Eds., Academic Press, incorporated herein by reference). The vectors typically comprise additional attached sequences which confer resistance to degradation of the nucleic acid fragment, which assist in the process of genomic integration, or which provide a means to easily select for those cells or plants which are transformed. Such sequences are advantageous and greatly decrease the difficulty of selecting useable transformed plants.

The recombinant vectors of the present invention typically comprise an expression cassette designed for initiating transcription of the desired nucleotide segments in plants. Companion sequences, of bacterial or viral origin, are also included to allow the vector to be cloned in a bacterial or phage host. The vector will preferably contain a broad host range prokaryote origin of replication. A selectable marker should also be included to allow selection of bacterial cells bearing the desired construct. Suitable prokaryotic selectable markers include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

For transcription in plants, the recombinant expression cassette will contain, in addition to the desired nucleic acid segment, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the transcription start site is called +1. Sequences extending in the 5' (upstream) direction are given negative numbers and sequences extending in the 3' (downstream) direction are given positive numbers.

In plants, further upstream from the TATA box, at positions -80 to -100, there is typically a promoter element with a series of adenines surrounding the trinucleotide G (or T) N G. J. Messing et al., in *Genetic Engineering in Plants*, pp. 221–227 (Kosage, Meredith and Hollaender, eds. 1983), which is incorporated herein by reference. Other sequences conferring tissue specificity, response to environmental signals, or maximum efficiency of transcription may also be found in the promoter region. Such sequences are often found within 400 bp of transcription start site, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The particular promoter used in the expression cassette is a noncritical aspect of the invention. Any of a number of promoters which direct transcription in plant cells is suitable. Promoters of bacterial origin include the octopine synthase promoter, the nopaline synthase promoter and other promoters derived from native Ti plasmids. Herrara-Estrella et al., *Nature*, 303:209–213, 1983. Viral promoters include the 35S and 19S RNA promoters of cauliflower mosaic virus. Odell et al. *Nature*, 313:810–812, 1985. Possible plant promoters include the ribulose-1,3-bisphosphate carboxylase small subunit promoter, the phaseolin promoter, and the E8 promoter. Promoters from genes which activated at the correct developmental stage in the target tissue are typically used. For instance, promoters active in flowers are known (Benfy, et al., *Plant Cell* 2:849–856 (1990), which is incorporated herein by reference). Promoters from genes induced in response to pathogens such as the lintinase promoter can also be used. (Roby, et al., *Plant Physiol.* 97:433–439 (1991) which is incorporated herein by reference).

The promoter can be either constitutive or inducible. A promoter which is expressed concurrently with or prior to the normal activation of the homologous endogenous sequence is preferred. A "constitutive" promoter is a promoter which is active under most environmental conditions and states of development or cell differentiation. An "inducible" promoter is a promoter which is under more precise environmental or developmental control. Examples of environmental conditions that may effect transcription by inducible promoters include anaerobic conditions or the presence of light. Examples of promoters under developmental control include promoters that initiate transcription only in response to ethylene, such as E8.

In addition to a promoter sequencer the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1:419–434, 1982. Polyadenylation sequences include, but are not limited to the Agrobacterium octopine synthase signal (Gielen et al., *EMBO J.*, 3:835–846, 1984) or the nopaline synthase signal (Depicker et al., *Mol. and Appl. Genet*, 1:561–573, 1982). In the present invention, the antisense sequences are not typically translated, however, thus polyadenylation should not be necessary.

The vector should also contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

The antisense nucleotide segment to be introduced generally will be homologous to the endogenous sequence intended to be repressed. As used herein "homologous" means corresponding to (the same as). One of skill will recognize, however, that exact correspondence between the introduced sequence and the sequence to be repressed is not required to effectively inhibit expression. Thus, the term "homologous" as used herein encompasses both complete and substantial homology between the two sequences. The minimal homology of the introduced sequence will typically be greater than about 65%, but a higher homology will usually exert a more effective repression of expression of the endogenous sequences. Substantially greater homology, or more than about 80% is preferred, though about 95% to absolute identity would be most preferred. Consequently, the effect should apply to any other genes within a similar family of genes exhibiting homology or substantial homology. For example, E8 is one of a number of homologous genes which comprise a gene family. Thus, repression of one member of the family will typically serve to impose the same repressive effect on others of the family. Similarly, for example, related genes from other plant species may also be utilized.

The term "substantial homology" as used herein refers to nucleotide sequences which share a majority of their sequence. Generally, this will be at least about 65% of their sequences and preferably about 95% of their sequence. Another indication that sequences are substantially homologous is if the complementary strand of one sequence hybridizes to the other sequence under stringent conditions. Stringent conditions will depend upon various parameters and will be different in different circumstances. Generally, stringent conditions are those in which the salt concentration is at least about 0.2 molar and the temperature is at least about 60° C.

The introduced sequence, needing less than absolute homology, also need not be full length, relative to either the primary transcription product or fully processed mRNA. A higher homology in a shorter than full length sequence compensates for a longer less homologous sequence. Furthermore, the introduced sequence need not have the same intron or exon pattern, and homology of non-coding segments will be equally effective. Normally, a sequence of between about 20 nucleotides and 100 nucleotides should be used, though a sequence of between about 100 and about 500 nucleotides is preferred, and a sequence of between about 500 and about 1000 nucleotides is especially preferred.

It should be noted that since a full length coding sequence is unnecessary, it is possible to produce the same effect on multiple proteins using a single transformation by fusing multiple sequences together to coordinately repress various different genes. In addition, assuming a sufficient number of introductions are made, the introduced sequence need not be linked to an operative promoter sequence. However, as discussed above, use of a promoter sequence is preferred.

4. Transcription of the Desired Antisense Nucleic Acid Segment in Plant Cells

A. Transformation of Plant Cells by In Vitro Techniques

1. Direct Transformation

The vectors described above can be microinjected directly into plant cells by use of micropipettes to mechanically transfer the recombinant DNA. Crossway, *Mol. Gen. Genetics*, 202:179–185 (1985), which is incorporated herein by reference. The genetic material may also be transferred into the plant cell using polyethylene glycol, Krens, et al., *Nature*, 296, 72–74, (1982), which is incorporated herein by reference.

Another method of introduction of nucleic acid segments is high velocity ballistic penetration by small particles with the nucleic acid either within the matrix of small beads or particles, or on the surface, Klein, et al., *Nature*, 327, 70–73 (1987), which is incorporated herein by reference.

Yet another method of introduction is fusion of protoplasts with other entities, either minicells, cells, lysosomes or other fusible lipid-surfaced bodies, Fraley, et al., *Proc. Natl. Acad. Sci. USA*, 79, 1859–1863 (1982), which is incorporated herein by reference.

The DNA may also be introduced into the plant cells by electroporation. Fromm et al., *Pro. Natl Acad. Sci. USA*, 82:5824 (1985), which is incorporated herein by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

2. Vectored Transformation

Cauliflower mosaic virus (CaMV) may be used as a vector for introducing the antisense DNA into plant cells. (Hohn et al., 1982 *"Molecular Biology of Plant Tumors,"* Academic Press, New York, pp.549–560; Howell, U.S. Pat. No. 4,407,956), which are incorporated herein by reference. In accordance with the described method, the entire CaMV viral DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

A preferred method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants.

Agrobacterium is a genus in the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science*, 237:1176–1183 (1987), which is incorporated herein by reference.

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid, such vectors are typically termed binary vectors. Hoekema, et al., *Nature,* 303:179–189 (1983), which is incorporated herein by reference. The transferred DNA region, can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors", (Ruvkun and Ausubel, 1981, Nature 298:85–88), promoters, (Lawton et al., 1987, Plant Mol. Biol. 9:315–324) and structural genes for antibiotic resistance as a selection factor (Fraley et al., *Proc. Nat. Acad. Sci.,* 80:4803–4807, 1983), all of which are incorporated herein by reference.

All plant cells which can be transformed by Agrobacterium and from which whole plants can be regenerated can be transformed according to the present invention to produce transformed intact plants which contain the desired DNA. There are two common ways to transform plant cells with Agrobacterium:

(1) co-cultivation of Agrobacterium with cultured isolated protoplasts, or (2) transformation of intact cells or tissues with Agrobacterium.

Method (1) requires an established culture system that allows for culturing protoplasts and subsequent plant regeneration from cultured protoplasts.

Method (2) requires (a) that the intact plant tissues, such as cotyledons, can be transformed by Agrobacterium and (b) that the transformed cells or tissues can be induced to regenerate into whole plants.

Most dicot species can be transformed by Agrobacterium. All species which are a natural plant host for Agrobacterium are transformable in vitro. Monocotyledonous plants, and in particular, cereals, are not natural hosts to Agrobacterium. There is growing evidence now that certain monocots can be transformed by Agrobacterium. Using novel experimental approaches cereal species such as rye (de la Pena et al., *Nature* 325:274–276, 1987), corn (Rhodes et al., *Science* 240:204–207, 1988), and rice (Shimamoto et al., *Nature* 338:274–276, 1989) may now be transformed, see also, Hooykas-Van Slogteren et al., Nature, 311:763–764 (1984), all of which are incorporated herein by reference.

B. Selection and Regeneration of Transformed Plant Cells

After transformation, transformed plant cells or plants comprising the antisense DNA must be identified. A selectable marker, such as those discussed, above, is typically used. Transformed plant cells can be selected by growing the cells on growth medium containing the appropriate antibiotic. The presence of opines can also be used if the plants are transformed with Agrobacterium.

After selecting the transformed cells, one can confirm transcription of the ant-sense sequence. Simple detection of mRNA encoded by the inserted DNA can be achieved by well known methods in the art, such as Northern blot hybridization. The inserted sequence can be identified by Southern blot hybridization, as well. See, e.g., Sambrook, supra.

After determination of the presence of the DNA, whole plant regeneration is desired. All plants from which protoplasts can be isolated and cultured to give whole regenerated plants can be transformed by the present invention. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Myoscyamus, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, cucumis, Browaalia, Glycine, Lolium, Zea, Triticum, Sorghum, Malus, Apium, and Datura.

Plant regeneration from cultured protoplasts is described in Evans et al., *Handbook of Plant Cell Cultures,* Vol. 1: (MacMillan Publishing Co. New York, 1983); and Vasil I. R. (ed.), *Cell Culture and Somatic Cell Genetics of Plants,* Acad. Press, Orlando, Vol. I, 1984, and Vol. III, 1986, which are incorporated herein by reference.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Regenerated plants with the desired characteristics are typically identified by determining the degree of response to ethylene. For instance, if the ethylene-mediated response is fruit ripening, delay in fruit ripening in response to exogenously applied ethylene can be measured. Particular ethylene-mediated responses which can be measured include, accumulation of pigments, fruit softening, and the like. In addition, Northern blot hybridization analysis can be used to detect levels of target mRNA in the transgenic plants.

While many of these improvements suggested above are not essential, the efficiency of production of useful transformants may be significantly affected. Some of the transformants may be identical to the parental plants, others may have decreased expression of the targeted gene in the fruit or other organs of interest. Others may have reduced expression levels in certain cells or patches of cells or segments of fruits or other organs resulting in regular or irregular patterns. Leaves on the same plant may even have different patterns. The likelihood of obtaining a desirable transformant will depend upon the number of plants screened and the efficiency of actual transformation and transcription of the antisense sequence.

In addition, a number of factors may affect expression of the introduced nucleic acid segment, including the type of promoter, the temporal pattern of the promoter, and the operation of the promoter in view of its position within the genome. It is well known that the operation of a promoter may vary depending on its location in the genome. Thus, an inducible promoter may operate differently in a different location, e.g., it may become fully or partially constitutive.

If the introduced nucleic acid segment is an intact gene from the target plant or other plant species (meaning a complete gene containing coding sequences, intron, promoter, enhancers and other cis-acting regulatory elements either upstream (5') or downstream (3') of the coding sequences), a fraction of independent transformed plants, may carry the introduced gene in locations that result in abnormal expression, i.e., expression at abnormal times in development. If the introduced gene is a chimeric gene (meaning that one or more elements, such as a promoter, from another gene has been substituted for a component of the intact gene or added to the intact gene, including coding sequences fused to upstream and downstream sequences necessary or beneficial for expression) and is driven by a constitutive (fully or partially) promoter, then abnormal levels and times of expression will be achieved in a large fraction of the transformed plants. If the introduced gene is a chimeric gene and is driven by a developmentally regulated promoter, depending on the promoter, some fraction of plants will show abnormal levels and times of expression of the introduced gene. The strength of the promoter or other cis element can be the same, lower, or higher than the coding sequence's usual promoter. The timing in development can be earlier or the same.

Finally, one of skill will recognize that after the expression cassette is stably incorporated in transgenic plants and confirmed to be operable, it can be introduced into other plants by sexual crossing. Any of a number of standard breeding techniques can be used, depending upon the species to be crossed.

DEFINITIONS

The phrases "nucleic acid sequence" or "nucleic acid segment" refer to a single or double-stranded polymer of deoxyribonucleotide or ribonucleotide bases read from the 5' to the 3' end. It includes both self-replicating plasmids, infectious polymers of DNA or RNA and non-functional DNA or RNA.

The term "promoter" refers to a region of DNA upstream from the structural gene and involved in recognition and binding RNA polymerase and other proteins to initiate transcription. A "plant promoter" is a promoter capable of initiating transcription in plant cells.

The term "plant" includes whole plants, plant organs (e.g., leaves, stems, roots, etc.), seeds and plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid. Plants from the genus Nicotiana are preferably used.

The phrase "suitable host" refers to a microorganism or cell that is compatible with a recombinant plasmid, DNA sequence or recombinant expression cassette and will permit the plasmid to replicate, to be incorporated into its genome, or to be expressed.

The term "expression" refers to the transcription and translation of a structural gene so that a protein is synthesized.

The term "antisense orientation" refers to the orientation of nucleic acid sequence from a structural gene that is inserted in an expression cassette in an inverted manner with respect to its naturally occurring orientation. When the sequence is double stranded, the strand that is the template strand in the naturally occurring orientation becomes the coding strand, and vice versa.

The term "uninterrupted" refers to a DNA sequence (e.g., cDNA) containing an open reading frame that lacks intervening, untranslated sequences.

The term "operably linked" refers to functional linkage between a promoter and a second sequence, wherein the promoter sequence initiates transcription of RNA corresponding to the second sequence.

A "heterologous sequence" or "heterologous expression cassette" is one that originates from a foreign species, or, if from the same species, is substantially modified from its original form.

The following examples are offered by way of illustration, not by way of limitation.

EXAMPLE 1

Identification of Ethylene-Inducible Sequences in Tomato Fruit

The methods used to isolate desired sequences are described in Lincoln et al., supra. Briefly, the methods are as follows:

Plant Material. *Lycopersicon esculentum* cv. VFNT Cherry plants were grown under standard greenhouse conditions. Fruit maturity stage was determined as follows. Immature fruits were 50% full size. Full size MG (Mature Green) stages were identified by the extent of locular tissue breakdown resulting in the formation of a viscous gel. Su et al., *Hortic. Sci.* 19:576–578 (1984), which is incorporated herein by reference. In MG1 fruit the locular tissue was firm, in MG2 fruit a small amount of gel was present, and in MG3 fruit the formation of the gel was complete. In MG4 fruit pigmentation was just detectable in the interior of the fruit, whereas later stages of fruit development were defined by further pigment accumulation.

Exposure of Fruit to Gasses. One kilogram of mature green fruit was placed in a 25-liter chamber and exposed to 4.5 liters per min. of humidified ethylene, in air (10 µl per liter) or to air alone.

mRNA Isolation. Pericap tissue was frozen in liquid nitrogen and stored at $-80°$ Polysomal, poly(A)$^+$ mRNA was isolated using procedures as described in Goldberg et al. *Dev. Biol.*, 83:201–217 (1981), which is incorporated herein by reference except that the EDTA-release step was omitted, and the polysome extraction buffer was adjusted to 160 mM KCl and 70 mM MgCl$_2$.

Constructing and Screening an Enriched cDNA Library. A cDNA library enriched for MG4-specific sequences was constructed using subtraction hybridization procedures of Davis et al., Supra. Seven micrograms of $^{32}$P-labeled MG4 cDNA and 70 µg of MG1 mRNA were hybridized for 16.5 hr at 70° C. in a 12 µl reaction containing 33 mM Pipes, pH 6.9/1M NaCl/0.2 mM EDTA/0.2% NaDodSO$_4$. Unreacted cDNA (12% of the total cDNA mass) was isolated by passing the reaction over a 1-ml hydroxyapatite column at 68° C. equilibrated in 0.12M NaH$_2$PO$_4$/0.12M Na$_2$HPO$_4$/0.2% NaDodSO$_4$. Enriched for MG4-specific sequences, the unreacted cDNA was used to construct a cDNA library. To screen the library, a probe enriched for ethylene-inducible sequences was isolated. $^{32}$P-labeled cDNA was synthesized using template mRNA isolated form MG1 fruit treated with exogenous ethylene for 8 hr. Two micrograms of this labeled cDNA was hybridized for 18 hr o 24 µg of MG1 mRNA in a 6 µl reaction, and the unreacted cDNA (10% of the total cDNA mass) was isolated by hydroxyapatite chromatography. Although the unreacted cDNA represented a 10-fold enrichment for ethylene-inducible sequences, it still contained a substantial amount of nonspecific sequences. We therefore constructed a control probe that represented only the nonspecific sequences. Two micrograms of $^{32}$P-labeled MG1 cDNA was hybridized to 24 μg of its own template mRNA, and the unreacted cDNA (9% of the total cDNA mass) was isolated by hydroxyapatite chromatography as described above. The MG4-enriched library was differentially screened by hybridizing replica clones to both probes as described in Graustein et al. *Proc. Natl. Acad. Sci. U.S.A.* 72:396–3965 (1975), which is incorporated herein by reference. Ethylene-inducible clones hybridized intensely to the probe enriched for ethylene-inducible sequences and hybridized weakly or not at all to the control probe.

Figure 1:
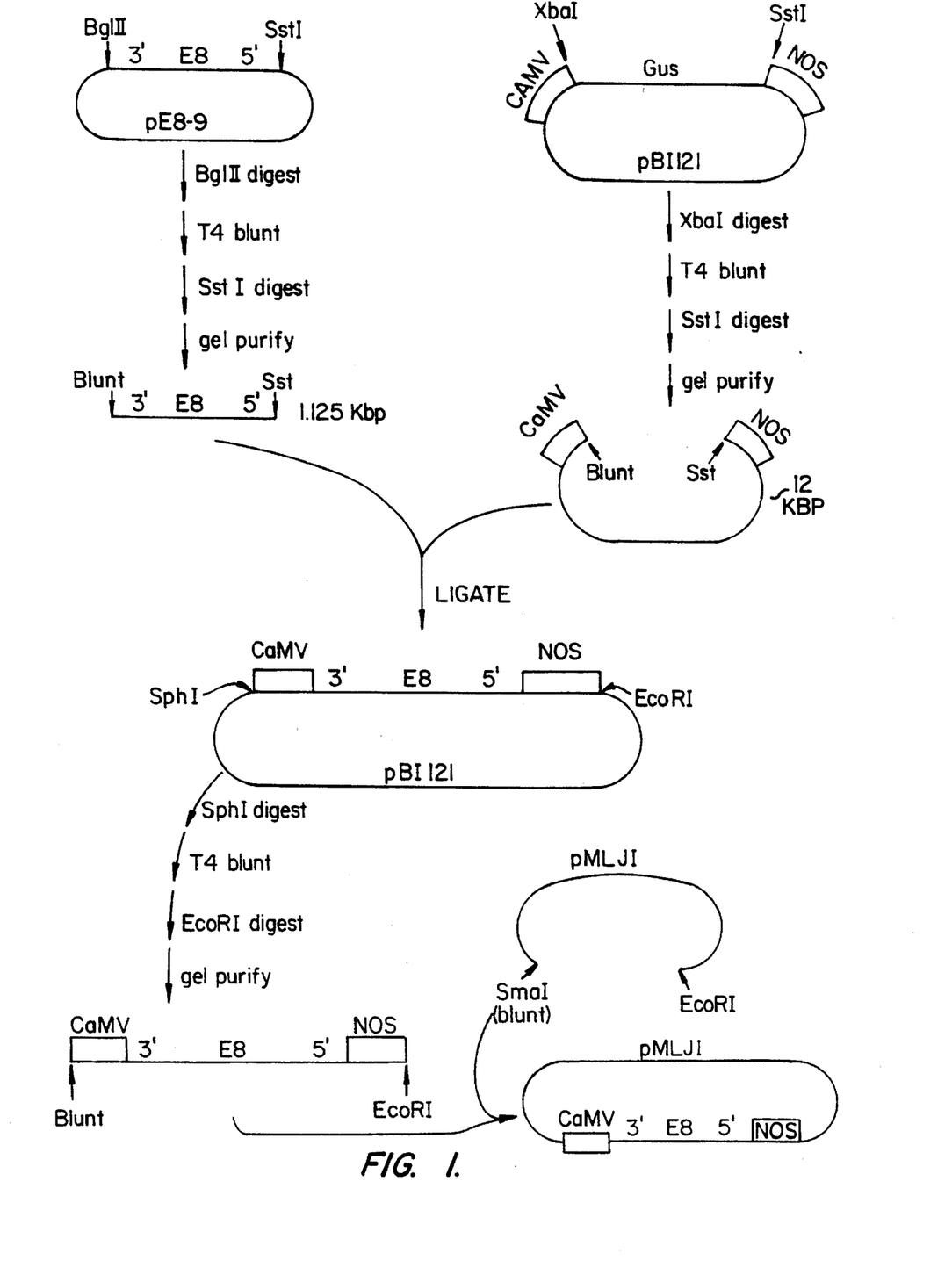
FIG. 1 shows construction of the expression cassette of the present invention.

Using these procedures we obtained three classes of ethylene-induced cDNA clones represented by E4, E8, and E17. We also selected from the MG4-enriched library a control cDNA clone, E41, that did not hybridize to the probe enriched for ethylene-inducible sequences. In addition, we identified a class of clones (designated J49) by using the same methods described above to screen a cDNA library derived from MG1 exposed to ethylene for 8 hr. FIG. 1 shows that each cDNA clone represents a distinct size mRNA. These results indicate that exposing MG1 tomato fruit to exogenous ethylene induces the expression of at least four different genes. As described in Lincoln et al. supra, the E41 gene probably encodes polygalacturonase and E17 encodes a proteinase inhibitor.

The vector was then used to transform tomato cotyledon pieces as described in copending application U.S. Ser. No. 07/511,417, which is incorporated herein by reference. The methods for regeneration of whole plants are the same as those in that application, as well.

EXAMPLE 2

Construction of an Expression Cassette and Transformation of Tomato

The sequence of an E8 genomic DNA clone (SEQ ID No. 1) is presented in Deikman and Fischer, *EMBO J.* 7:3315–3320 (1988), which is incorporated herein by reference. An expression cassette comprising antisense E8 cDNA identical to the coding regions of the genomic clone has been deposited with ATCC, Rockville, Md., on Oct. 8, 1991 and has Deposit No. 68753. The gene in FIG. 1 was constructed as follows. The E8 cDNA clone was digested with Bgl II, the Bgl II ends were made blunt with T4 DNA polymerase, the plasmid was digested with Sst I, and the 1.125 kbp restriction fragment containing the E8 coding sequences was gel purified. Next, plasmid pBI121 (purchased from Clontech catalog number 6018-1; containing a 35S CaMV promoter ligated to --glucuronidase coding sequences plus nopaline synthase transcription terminator sequences) was digested with Xba I, the Xba I ends were made blunt with T4 DNA polymerase, the plasmid was digested with Sst I, and the ≈12 kbp restriction fragment containing the vector plus the CaMV promoter and Nos terminator sequences was gel purified. Finally, the E8 coding sequences were inserted in the antisense orientation between the CaMV promoter and the Nos terminator sequences by ligating the 1.125 kbp restriction fragment with the 12 kbp restriction described above.

To move the E8 antisense expression cassette (CaMV+E8 antisense+Nos) into the Agrobacterium tumefaciens shuttle vector pMLJ1 (see, DeBloch, et al., *EMBO J.* 3:1681–1689 (1984), which is incorporated herein by reference), we did the following. pBI121 containing the E8 antisense gene was digested with Sph I, the Sph I ends were made blunt with T4 DNA polymerase, the plasmid was digested with Eco RI, and the ≈2.2 kbp restriction fragment containing E8 antisense gene was gel purified. pMLJ1 was digested with Sma I (natural blunt end) and Eco RI and the ≈6.95 kbp vector restriction fragment was gel purified. The 2.2 and 6.95 kbp restriction fragments described above were ligated and used to transform *E. coli*. The construction of the cassette is illustrated in FIG. 1.

EXAMPLE 3

Demonstration that E8 Expression is Inhibited

Figure 2:
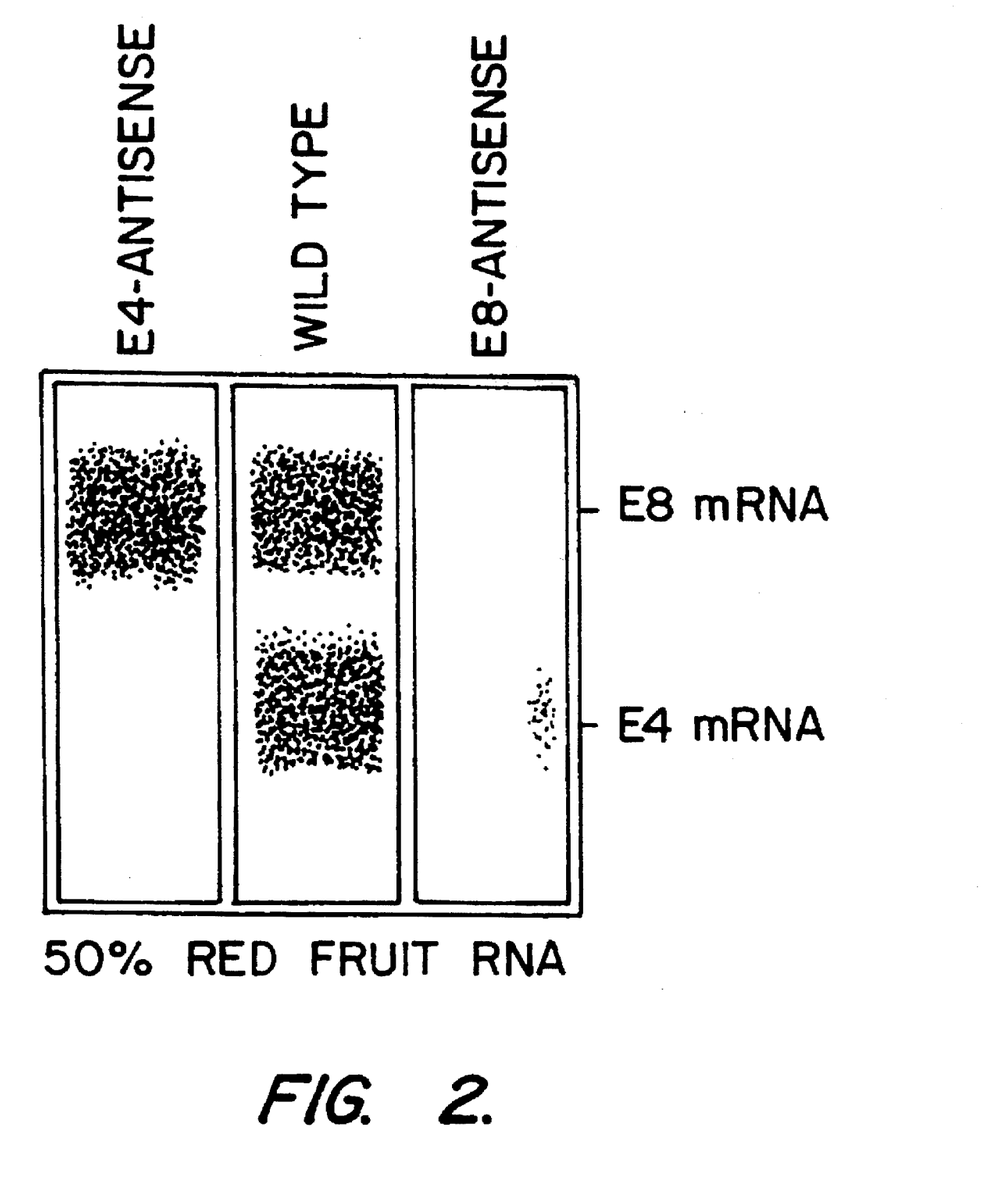
FIG. 2 is a Northern blot hybridization demonstrating inhibition of expression of E8 in transgenic plants comprising the expression cassette of the invention.

To find a transgenic (bearing the CaMV-E8 antisense gene) plant with low level expression of the E8 gene, we isolated total RNA from tomato fruit (harvested at 50% red stage) using procedures described in Giovannoni, J. J. et al. *The Plant Cell*, 1, 53–63 (1989), which is incorporated herein by reference. The RNA was denatured, subjected to agarose gel electrophoresis (20 μg per lane), blotted hybridized with labeled probe as described (Ausubel, F. M., et al. in *Current Protocols in Molecular Biology*, (Greene Publishing Associates & Wiley-Interscience, New York, 1989), which is incorporated herein by reference. The probe used was E8 and E4 sequences. The results are presented in FIG. 2. As expected, control wild type fruit has both E4 and E8 mRNAs. In addition, we found that a control E4 antisense plant does not accumulate E4 mRNA. The E8 antisense plant has reduced levels of E4 mRNA because it is insensitive to ethylene.

EXAMPLE 4

Figure 3:
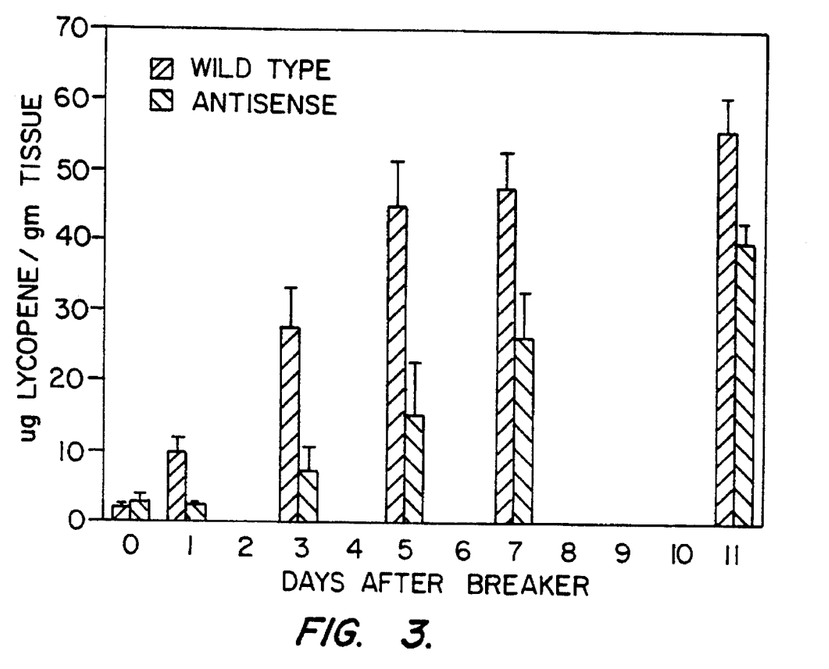
FIG. 3 illustrates that incubation of E8 gene expression slows red lycopene pigment accumulation in transgenic tomato fruit.

Inhibition of E8 Expression Inhibits a Number of Ethylene-Mediated Responses A. Lycopene Accumulation To determine if lycopene accumulation was slowed by inhibition of E8 gene expression, we measured lycopene levels in transgenic and control (wild type) fruit using procedures described by Smith et al., *Nature* 334:724–726 (1988) which is incorporated herein by reference. Fruit were harvested at the onset of ripening (breaker stage) and stored at 28° C. At the indicated days after harvest, fruit tissue was frozen and stored at −80C. To this end, 1 gm of tissue was ground three times in 20 ml of hexane:acetone (6:4) in a polytron homogenizer. Debris was removed by centrifugation. The level of lycopene in the supernatant was determined spectrophometrically as described in Smith, et al. Results, shown in FIG. 3, represent the mean ± standard error. A minimum of 3 transgenic and 3 wild type fruit were tested for each time point.

B. Fruit Softening

Figure 4:
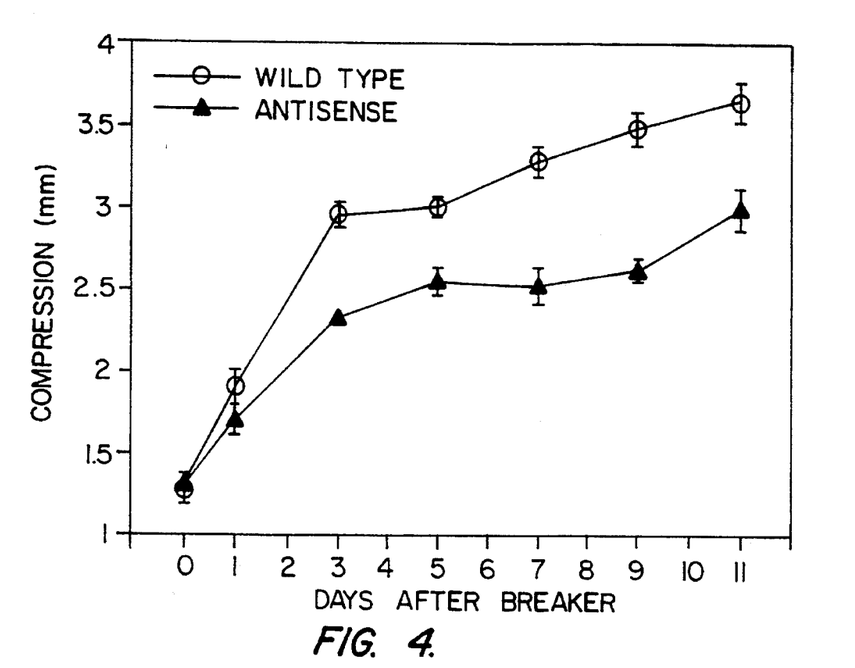
FIG. 4 illustrates that inhibition of E8 gene expression retards softening in transgenic tomato fruit.

We wanted to determine if inhibition of E8 gene expression resulted in increased fruit firmness. To this end, transgenic and control (wild type) fruit were harvested at the onset of ripening (breaker stage) and stored at 28° C. At the indicated days after harvest, softening was measured by extent of compression of the fruit when subjected to a 500 gm weight for 10 seconds as described in Brady et al., *J. Food Biochem*, 7:7–14 (1983), which is incorporated herein by reference. Results presented in FIG. 4, represent the mean ± standard error. A minimum of 10 transgenic and 10 wild type fruit were tested for each time point.

C. Rate of Fruit Ripening

A transgenic fruit and a wild type fruit were harvested at the onset of ripening (breaker stage) and stored at 28° C. Four days after harvest the color of the fruit was compared. Fruit from transgenic plants remained substantially green, whereas fruit from wild type plants had turned entirly red.

EXAMPLE 5

E8 Antisense Gene Segregates with Elevated Ethylene Production

Figure 5:
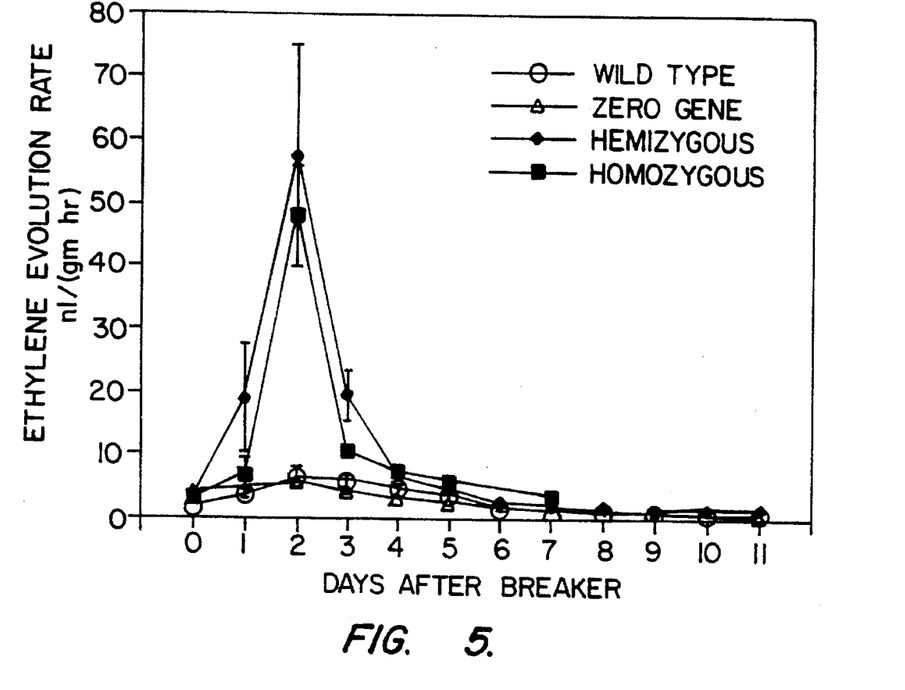
FIG. 5 illustrates that inhibition of E8 gene expression produces elevated levels of ethylene in transgenic tomato fruit.

We wanted to determine if ethylene insensitive tomato fruit produce elevated levels of ethylene. In this regard, it had previously been reported that ethylene insensitive Arabidopsis mutants produce elevated levels of ethylene (Guzman and Ecker, *The Plant Cell* 2:513–523 (1990)). To this end, fruit were harvested at the onset of ripening (breaker stage) and stored at 28° C. At the indicated days after harvest, individual fruits were placed in 500 ml containers that were sealed and incubated at room temperature for 1 hour. A 1 ml sample from the closed atmosphere was removed, and the ethylene content was determined by gas chromatography, according to standard techniques (Hach/Carle). Results, presented in FIG. 5, represent the mean ± standard error. Wild type, non transformed fruit; Hemizygous, the original E8 antisense transformant that has one copy of the E8 antisense locus; Homozygous, progeny of the original transformed plant that have 2 copies of the E8 antisense locus; Zero gene, progeny of the original transformed plant that have 0 copies of the E8 antisense locus.

Figure 6:
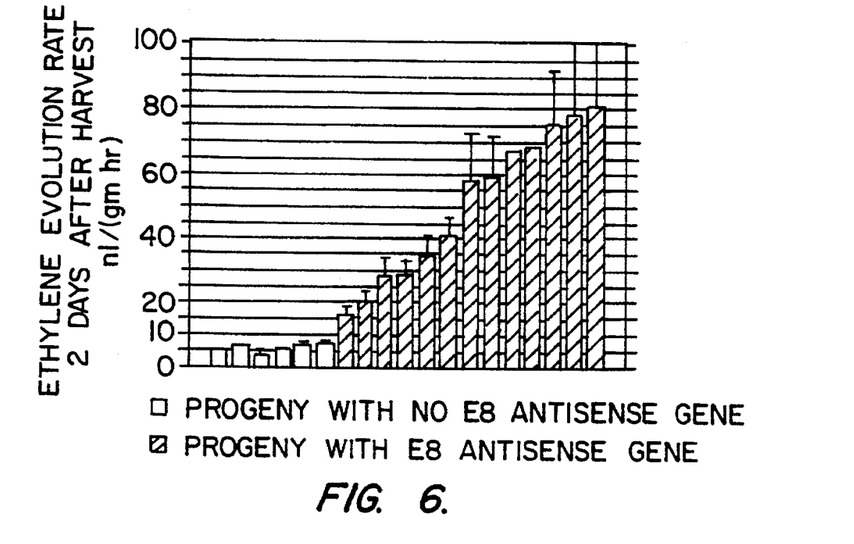
FIG. 6 illustrates that the E8 antisense gave segregates with elevated ethylene production.

We wanted to know if the elevated ethylene production, noted above, segregates with the E8 antisense locus. To this end we collected seed from the original transformed hemizygous plant that contains one E8 antisense locus. 19 progeny plants were generated and the presence or absence of the E8 locus was determined by blot hybridization experiments. As expected, approximately 25% of the progeny (6/19) did not have the E8 antisense locus. For each progeny plant, fruit were harvested at the onset of ripening (breaker stage) and stored at 28° C. At the indicated days after harvest, individual fruits were placed in 500 ml containers that were sealed and incubated at room temperature for 1 hour. A 1-ml sample from the closed atmosphere was removed, and the ethylene content was determined by gas chromatography (Hach/Carle). Results, presented in FIG. 6, represent the mean ± standard error.

What is claimed is:

1. A tomato plant comprising a heterologous expression cassette comprising a plant promoter sequence operably linked to a nucleotide sequence comprising a substantially full length E8 gene, wherein the nucleotide sequence is linked to the promoter sequence in an antisense orientation.

2. The plant of claim 1, wherein the nucleotide segment is uninterrupted by introns.

3. The plant of claim 1, wherein the promoter is inducible.

4. A tomato plant comprising a heterologous expression cassette comprising a plant promoter sequence operably linked to a nucleotide sequence comprising a substantially full length E8 gene, wherein the nucleotide segment is linked to the promoter sequence in an antisense orientation, whereby transcription of the nucleotide segment inhibits fruit ripening.

5. A method for inhibiting fruit ripening in a tomato plant, the method comprising introducing into the plant an expression cassette having a plant promoter sequence operably linked to a nucleotide sequence comprising a substantially full length E8 gene, wherein the nucleotide sequence is linked to the promoter sequence in an antisense orientation.

6. The method of claim 5, wherein the nucleotide segment is uninterrupted by introns.

7. The method of claim 5, wherein the promoter is inducible.

8. The method of claim 5, wherein the expression cassette is introduced into the plant using Agrobacterium.

9. The method of claim 5, wherein the expression cassette is introduced into the plant by a sexual cross.

10. An expression cassette comprising a plant promoter sequence operably linked to a nucleotide sequence comprising a substantially full length E8 gene, wherein the nucleotide segment is linked to the promoter sequence in an antisense orientation.

11. The expression cassette of claim 10, wherein the promoter is inducible.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 2964 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: exon
( B ) LOCATION: 1044..1562

( i x ) FEATURE:
( A ) NAME/KEY: exon
( B ) LOCATION: 1983..2305

( i x ) FEATURE:
( A ) NAME/KEY: exon
( B ) LOCATION: 2381..2630

( x i ) SEQUENCE DESCRIPTION: SEQ ID NO:1:

```
CTAGAAGGAA    TTTCACGAAA    TCGGCCCTTA    TTCAAAAATA    ACTTTTAAAT    AATGAATTTT         60

AAATTTTAAG    AAATAATATC    CAATGAATAA    ATGACATGTA    GCATTTTACC    TAAATATTTC        120

AACTATTTTA    ATCCAATATT    AATTTGTTTT    ATTCCCAACA    ATAGAAAGTC    TTGTGCAGAC        180

ATTTAATCTG    ACTTTTCCAG    TACTAAATAT    TAATTTTCTG    AAGATTTTCG    GGTTTAGTCC        240

ACAAGTTTTA    GTGAGAAGTT    TTGCTCAAAA    TTTTAGGTGA    GAAGGTTTGA    TATTTATCTT        300

TTGTTAAATT    AAGGTGTATA    TGATGAAGGA    ATAAACAAGT    TCAGTGAAGT    GATTAAAATA        360

AAATATAATT    TAGGTGTACA    TCAAATAAAA    ACCTTAAAGT    TTAGAAAGGC    ACCGAATAAT        420
```

-continued

| | | | | | |
|---|---|---|---|---|---|
|TTTGCATAGA|AGATATTAGT|AAATTTATAA|AAATAAAAGA|AATGTAGTTG|TCAAGTTGTC 480|
|TTCTTTTTTT|TGGATAAAAA|TAGCAGTTGG|CTTATGTCAT|TCTTTTACAA|CCTCCATGCC 540|
|ACTTGTCCAA|TTGTTGACAC|TTAACTAATT|AGTTGATTC|ATGTATGAAT|ACTAAATAAT 600|
|TTTTTAGGAC|TGACTCAAAT|ATTTTTATAT|TATCATAGTA|ATATTTATCT|AATTTTTAGG 660|
|ACCACTTATT|ACTAAATAAT|AAATTAACTA|CTACTATATT|ATTGTTGTGA|ACAACAACG 720|
|TTTTGGTTGT|TATGATGAAA|CGTACACTAT|ATCAGTATGA|AAAATTCAAA|ACGATTAGTA 780|
|TAAATTATAT|TGAAAATTTG|ATATTTTCT|ATTCTTAATC|AGACGTATTG|GGTTTCATAT 840|
|TTTAAAAAGG|GACTAAACTT|AGAAGAGAAG|TTTGTTTGAA|ACTACTTTTG|TCTCTTTCTT 900|
|GTTCCCATTT|CTCTCTTAGA|TTTCAAAAAG|TGAACTACTT|TATCTCTTTC|TTTGTTCACA 960|
|TTTTATTTTA|TTCTATTATA|AATATGGCAT|CCTCATATTG|AGATTTTTAG|AAATTATTCT 1020|
|AATCATTCAC|AGTGCAAAAG|AAGATGGAAA|GCCCTAGAGT|TGAGGAGAGT|TATGACAAAA 1080|
|TGAGTGAATT|AAAAGCGTTT|GATGATACTA|AGGCCGGTGT|TAAAGGACTT|GTTGATTCTG 1140|
|GAATTACTAA|AGTACCTCAA|ATATTCGTTC|TACCGCCAAA|AGACAGGGCT|AAAAAATGTG 1200|
|AAACACATTT|CGTTTTCCA|GTGATAGACC|TTCAAGGTAT|CGATGAGGAT|CCGATTAAGC 1260|
|ATAAGGAGAT|AGTGGACAAA|GTTCGAGATG|CATCGGAGAA|ATGGGGTTTT|TTCCAAGTGG 1320|
|TTAATCATGG|GATTCCAACA|TCCGTCTTGG|ACAGAACGTT|GCAAGGAACA|CGACAGTTCT 1380|
|TTGAGCAAGA|TAACGAGGTT|AAGAAACAGT|ATTACACTCG|AGATACTGCG|AAAAAGTGG 1440|
|TTTATACTAG|CAATCTTGAT|TTGTATAAAT|CTTCTGTTCC|AGCTGCAAGT|TGGAGAGACA 1500|
|CGATTTTCTG|TTACATGGCT|CCGAATCCTC|CCAGTCTACA|AGAATTTCCA|ACTCCATGCG 1560|
|GGTAAGTATT|TTCATTTCTT|AGTCTGGAGA|TTCTTTAGTA|GCTCAGTGGC|AGAGGCGGAC 1620|
|CCTCCGCCGT|GCTCGAGCAC|CCATTAATTT|CGTTACGGAA|TATATATATA|TCTACGTAGA 1680|
|AATTAATATG|TATTTGTATA|AAATTAACAT|AGAGCACCCA|ATGAATAAAC|GATTTAGTTG 1740|
|GCCCAATGGC|TCCTGGATGA|ATACTCTGTT|AACACATATT|TTTTATATTT|TCAGTTTAAA 1800|
|TTTCTAGATC|CGCCACTGCT|CAGTTGATTG|ACTATCTAAA|GACAGCAAAA|ATTCCTAGAT 1860|
|CTGTCGCTGC|TCAGTTGATT|GAGTATCTAA|ATACAGCAAA|TTCTTAGATC|CGCCATTGCT 1920|
|TAGTTGATTG|ACTATCTAAA|GACGTCTGAT|TTTATATAAA|AATATGTCAT|GTTTCAATGC 1980|
|AGGGAGTCAT|TAATAGACTT|CTCCAAGGAT|GTGAAGAAAC|TGGGATTCAC|TTTACTTGAA 2040|
|TTATTGTCTG|AAGGTCTCGG|TCTCGATCGT|AGTTATCTCA|AGATTATAT|GGATTGTTTT 2100|
|CATCTTTTCT|GTTCTTGCAA|CTACTACCCA|CCATGTCCTC|AGCCAGAACT|CACCATGGGC 2160|
|ACCATTCAAC|ATACCGATAT|TGGTTTTGTA|ACGATCCTTC|TACAAGATGA|TATGGGAGGG 2220|
|CTCCAAGTTC|TTCACCAGAA|TCATTGGGTT|GATGTTCCTC|CTACACCCGG|TTCTCTAGTG 2280|
|GTGAATATTG|GAGATTTTCT|GCAGGTTAGT|AGTCGATATT|ATATACAAAG|TTTATCGCGC 2340|
|AACACATTTA|GAAAATCTTT|TTTTTAATTA|TTTTTTGCAG|CTCTTGTCAA|ATGACAAGTA 2400|
|CTTAAGTGTC|GAGCACAGAG|CAATCTCAAA|CAATGTTGGA|TCAAGAATGT|CAATCACGTG 2460|
|CTTCTTCGGT|GAAAGTCCAT|ATCAATCTTC|CAAGCTTTAT|GGACCGATAA|CTGAATTGTT 2520|
|ATCAGAAGAT|AATCCTCCAA|AATATCGCGC|AACCACAGTG|AAAGACCACA|CTAGTTACCT 2580|
|CCATAACAGA|GGCCTAGATG|GAACTTCTGC|ATTGTCCCGT|TACAAGATCT|AAGAATAAGA 2640|
|ATAATAATGT|TATCTATTAT|TACTATTTAT|ACTTCTGCAG|ATTGTACCTT|TGAATTTGAA 2700|
|GCAAATGTTT|GAGTTAAATA|CTTTCACGTT|TCTAAGCAAT|GTAATATAAT|TTATAAAGTA 2760|
|TGTGCTTGCT|ATATATTGTT|GTTTAAAACA|TTAAATAATA|TTACATAAAT|ATAAACACCA 2820|

```
TAATATAAGG ATGTTTAGCA TTGTGGGAAA ATGAAGGATT AATAAGTCAT ATTAGTATTT      2880

CTCTATGTCA CATAAATGTG CCTTCAACTC AATTTCCGCT GATATTTATC TTCTTTTATT      2940

TTAAGTAGAC GCTTAAACTA TTGT                                            2964
```

( 2 ) INFORMATION FOR SEQ ID NO:2:

( i ) SEQUENCE CHARACTERISTICS:
        ( A ) LENGTH: 363 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | Ser | Pro | Arg | Val | Glu | Glu | Ser | Tyr | Asp | Lys | Met | Ser | Glu | Leu |
| 1 | | | | 5 | | | | | 10 | | | | | 15 | |
| Lys | Ala | Phe | Asp | Asp | Thr | Lys | Ala | Gly | Val | Lys | Gly | Leu | Val | Asp | Ser |
| | | | 20 | | | | 25 | | | | | 30 | | | |
| Gly | Ile | Thr | Lys | Val | Pro | Gln | Ile | Phe | Val | Leu | Pro | Pro | Lys | Asp | Arg |
| | | 35 | | | | | 40 | | | | | 45 | | | |
| Ala | Lys | Lys | Cys | Glu | Thr | His | Phe | Val | Phe | Pro | Val | Ile | Asp | Leu | Gln |
| | 50 | | | | | 55 | | | | | 60 | | | | |
| Gly | Ile | Asp | Glu | Asp | Pro | Ile | Lys | His | Lys | Glu | Ile | Val | Asp | Lys | Val |
| 65 | | | | | 70 | | | | | 75 | | | | | 80 |
| Arg | Asp | Ala | Ser | Glu | Lys | Trp | Gly | Phe | Phe | Gln | Val | Val | Asn | His | Gly |
| | | | | 85 | | | | | 90 | | | | | 95 | |
| Ile | Pro | Thr | Ser | Val | Leu | Asp | Arg | Thr | Leu | Gln | Gly | Thr | Arg | Gln | Phe |
| | | | 100 | | | | | 105 | | | | | 110 | | |
| Phe | Glu | Gln | Asp | Asn | Glu | Val | Lys | Lys | Gln | Tyr | Tyr | Thr | Arg | Asp | Thr |
| | | 115 | | | | | 120 | | | | | 125 | | | |
| Ala | Lys | Lys | Val | Val | Tyr | Thr | Ser | Asn | Leu | Asp | Leu | Tyr | Lys | Ser | Ser |
| | 130 | | | | | 135 | | | | | 140 | | | | |
| Val | Pro | Ala | Ala | Ser | Trp | Arg | Asp | Thr | Ile | Phe | Cys | Tyr | Met | Ala | Pro |
| 145 | | | | | 150 | | | | | 155 | | | | | 160 |
| Asn | Pro | Pro | Ser | Leu | Gln | Glu | Phe | Pro | Thr | Pro | Cys | Gly | Glu | Ser | Leu |
| | | | | 165 | | | | | 170 | | | | | 175 | |
| Ile | Asp | Phe | Ser | Lys | Asp | Val | Lys | Lys | Leu | Gly | Phe | Thr | Leu | Leu | Glu |
| | | | 180 | | | | | 185 | | | | | 190 | | |
| Leu | Leu | Ser | Glu | Gly | Leu | Gly | Leu | Asp | Arg | Ser | Tyr | Leu | Lys | Asp | Tyr |
| | | 195 | | | | | 200 | | | | | 205 | | | |
| Met | Asp | Cys | Phe | His | Leu | Phe | Cys | Ser | Cys | Asn | Tyr | Tyr | Pro | Pro | Cys |
| | 210 | | | | | 215 | | | | | 220 | | | | |
| Pro | Gln | Pro | Glu | Leu | Thr | Met | Gly | Thr | Ile | Gln | His | Thr | Asp | Ile | Gly |
| 225 | | | | | 230 | | | | | 235 | | | | | 240 |
| Phe | Val | Thr | Ile | Leu | Leu | Gln | Asp | Asp | Met | Gly | Gly | Leu | Gln | Val | Leu |
| | | | | 245 | | | | | 250 | | | | | 255 | |
| His | Gln | Asn | His | Trp | Val | Asp | Val | Pro | Pro | Thr | Pro | Gly | Ser | Leu | Val |
| | | | 260 | | | | | 265 | | | | | 270 | | |
| Val | Asn | Ile | Gly | Asp | Phe | Leu | Gln | Leu | Leu | Ser | Asn | Asp | Lys | Tyr | Leu |
| | | 275 | | | | | 280 | | | | | 285 | | | |
| Ser | Val | Glu | His | Arg | Ala | Ile | Ser | Asn | Asn | Val | Gly | Ser | Arg | Met | Ser |
| | 290 | | | | | 295 | | | | | 300 | | | | |
| Ile | Thr | Cys | Phe | Phe | Gly | Glu | Ser | Pro | Tyr | Gln | Ser | Ser | Lys | Leu | Tyr |
| 305 | | | | | 310 | | | | | 315 | | | | | 320 |
| Gly | Pro | Ile | Thr | Glu | Leu | Leu | Ser | Glu | Asp | Asn | Pro | Pro | Lys | Tyr | Arg |

|   |   |   | 325 |   |   |   |   | 330 |   |   |   |   | 335 |   |
|---|---|---|---|---|---|---|---|---|---|---|---|---|---|---|
| Ala | Thr | Thr | Val | Lys | Asp | His | Thr | Ser | Tyr | Leu | His | Asn | Arg | Gly | Leu |
|   |   |   | 340 |   |   |   |   | 345 |   |   |   |   | 350 |   |
| Asp | Gly | Thr | Ser | Ala | Leu | Ser | Arg | Tyr | Lys | Ile |   |   |   |   |
|   |   | 355 |   |   |   |   | 360 |   |   |   |   |   |   |   |